United States Patent [19]

Kugler et al.

[11] 4,206,135

[45] Jun. 3, 1980

[54] CATALYST COMPRISING NICKEL SUPPORTED ON TANTALUM OXIDE OR NIOBIUM OXIDE AND THEIR USE AS HYDROCARBON SYNTHESIS CATALYSTS IN CO/H$_2$ REACTIONS

[75] Inventors: Edwin L. Kugler, Summit; Samuel J. Tauster, Englishtown, both of N.J.

[73] Assignee: Exxon Research & Engineering Co., Florham Park, N.J.

[21] Appl. No.: 19,353

[22] Filed: Mar. 12, 1979

[51] Int. Cl.$^2$ .................................................. C07C 1/04
[52] U.S. Cl. ..................... 260/449.6 R; 260/449.6 M; 252/456; 252/444; 252/463; 252/473; 252/474
[58] Field of Search ................. 260/449.6 R, 449.6 M

[56] References Cited

U.S. PATENT DOCUMENTS

| | | | |
|---|---|---|---|
| 3,158,567 | 11/1964 | Cole et al. | 208/143 |
| 3,228,892 | 11/1966 | Cole et al. | 252/463 |

FOREIGN PATENT DOCUMENTS 2306 of 1914 United Kingdom .................. 260/449.6

*Primary Examiner*—Howard T. Mars
*Attorney, Agent, or Firm*—Joseph J. Allocca

[57] ABSTRACT

An improved method for the enhanced synthesis of paraffinic hydrocarbons with chain lengths of from 2 to 6 carbon atoms inclusive with reduced methane formation which method comprises the steps of passing a synthesis gas stream comprising CO and H$_2$ over a catalyst at a temperature and pressure for a time sufficient to generate the desired C$_2$–C$_6$ paraffinic product, wherein the catalyst comprises from about 0.01 to about 15 wt. % nickel on a support selected from the group consisting of tantalum oxides, niobium oxides, and other tantalum or niobium containing oxides and mixtures thereof. The nickel average crystallite size is preferably less than 5 nm (50 Å). The supported nickel catalyst has a BET surface area of from about 10 to 60 m$^2$/g.

15 Claims, 2 Drawing Figures

CATALYST COMPRISING NICKEL SUPPORTED ON TANTALUM OXIDE OR NIOBIUM OXIDE AND THEIR USE AS HYDROCARBON SYNTHESIS CATALYSTS IN CO/H₂ REACTIONS

BACKGROUND OF THE INVENTION

This invention relates to a new and improved Fischer-Tropsch hydrocarbon synthesis process utilizing a catalyst of nickel on tantalum oxide or niobium oxide or tantalum or niobium containing oxide supports, or mixtures thereof. This catalyst has a number of desirable characteristics, particularly increased selectivity to $C_2$-$C_6$ paraffins, reduced methane formation, improved CO conversions, a 2-fold increase in the rate of hydrocarbon formation per gram nickel and a 10-fold increase in specific rate.

Conventional state of the art nickel catalysts, i.e., nickel on alumina, nickel on silica, are well-known for their selectivity toward methane formation—for example, see M. Greyson, "Catalysis," Vol. IV 473 (1956) and H. A. Dirksen and H. R. Linden, Research Bulletin No. 31, Institute of Gas Technology (1963) and Shultz et al, Report of Investigations, 6974, Bureau of Mines, 1967, Pages 1-8. Within a wide range of temperature, pressure and $H_2$/CO mole rations, methane is by far the predominant hydrocarbon product, and it is the fact that has made nickel the catalyst of choice for commercial methane synthesis from CO and $H_2$.

DESCRIPTION OF THE INVENTION

Figure 1:
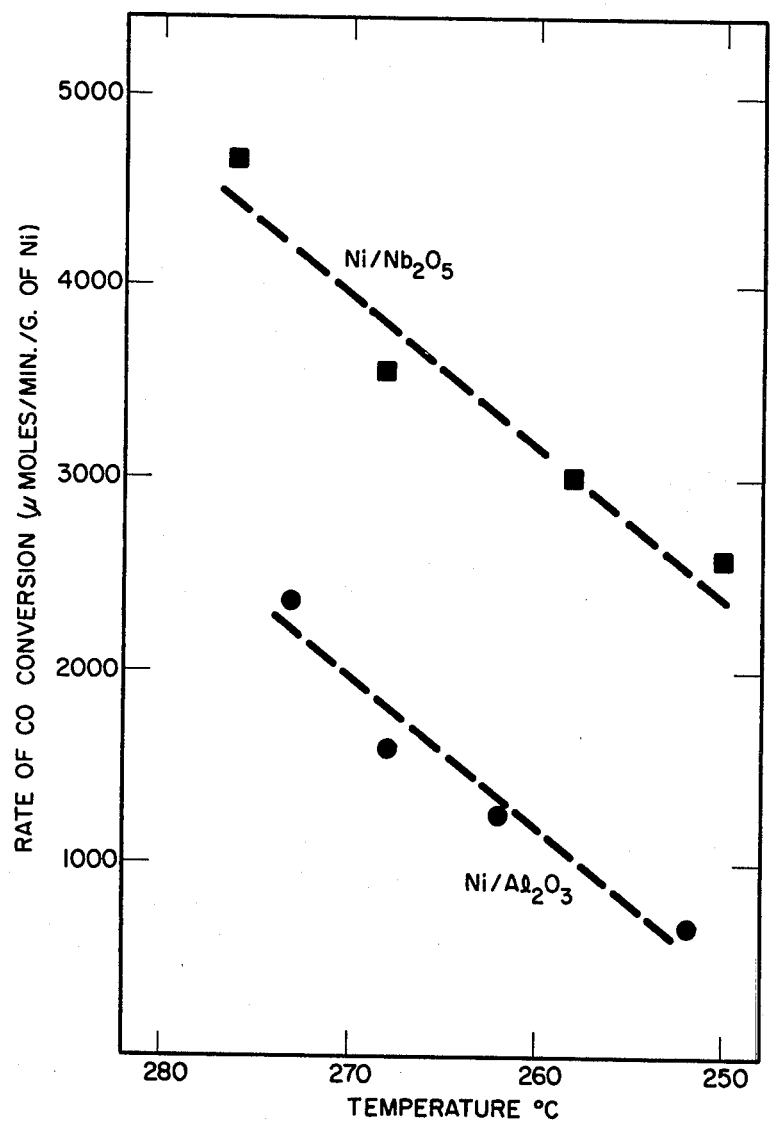
FIG. 1 presents a comparison of the activity of a Ni/$Nb_2O_5$ catalyst of the instant invention with a prior art catalyst for CO conversion.
Figure 2:
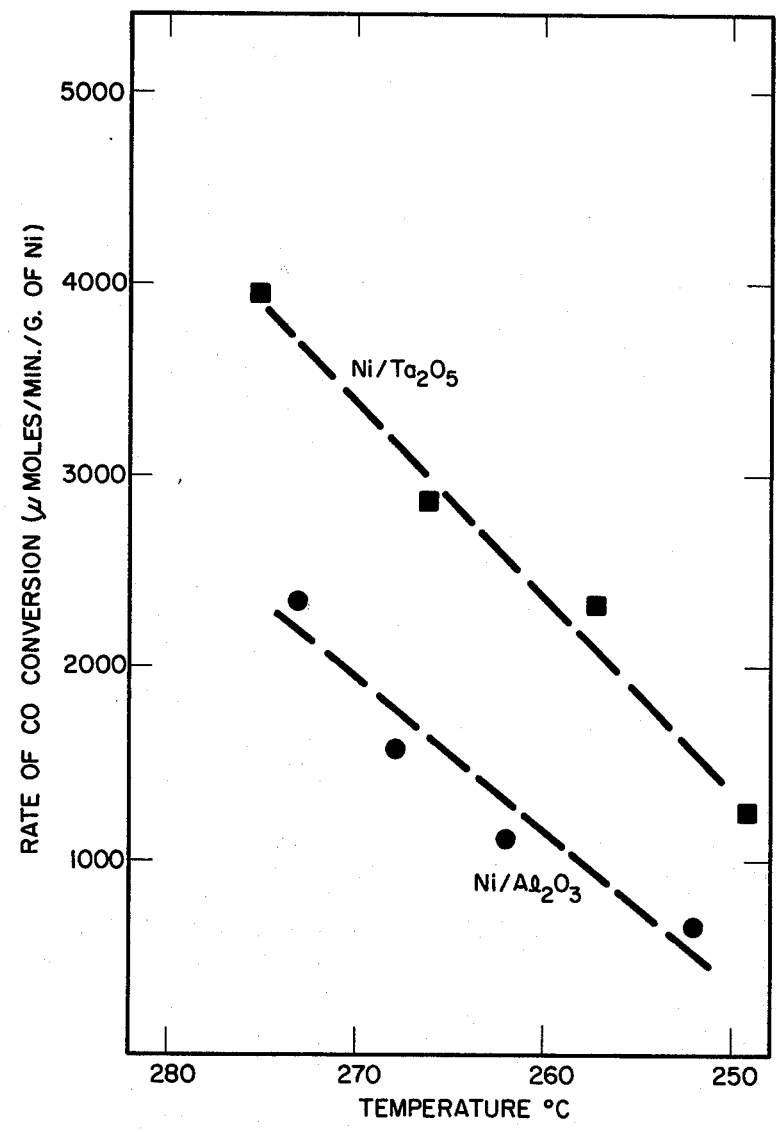
FIG. 2 presents a comparison of the activity of a Ni/$Ta_2O_5$ catalyst of the instant invention with a prior art catalyst for CO conversion.

A new method is disclosed for the selective synthesis of higher molecular weight normal paraffins or from 2-6 carbons inclusive from CO and $H_2$ over a wide range of CO conversions at pressures of from about 100 to $1 \times 10^5$ kPa which method comprises the steps of passing a synthesis gas stream comprising CO and $H_2$ over a catalyst comprising nickel supported on tantalum oxide, niobium oxide, other tantalum or niobium oxides or mixtures thereof at typical Fischer-Tropsch conditions for a time sufficient to effect the generation of the desired paraffinic products. Typically, the synthesis gas stream of CO and $H_2$ has an $H_2$/CO mole ratio of from about 0.1 to about 10, preferably about 0.5 to 4, most preferably about 1 to 3. This synthesis gas is typically passed over the catalyst at a space velocity of from about 100 hr$^{-1}$ to about 50,000 hr$^{-1}$. The typical reaction temperature ranges from about 100° to about 500° C., preferably about 150° to about 400° C., most preferably 150° to about 300° C., and a pressure of from about 100 to about $1.0 \times 10^5$ kPa, preferably about 100 to about 3100 kPa, most preferably about 100 to about 2100 kPa. The supported nickel catalyst system used in the process has a nickel loading ranging from about 0.01 to about 75 wt. % nickel on support and has a total BET nickel surface area of from 10 to 60 m²/g$^{-1}$ with a nickel crystallite size of less than 5 nm (50 Å). Preferably the nickel loading ranges from about 0.01 to about 30 wt. %, more preferably about 0.1 to about 15 wt. %, most preferably about 0.1 to about 5.0 wt. % nickel on the support.

Nickel supported on $Ta_2O_5$, $Nb_2O_5$, other tantalum or niobium-containing oxides or mixtures of tantalum or niobium-containing oxides results in a catalyst system which exhibits superior hydrocarbon synthesis characteristics. The tantalum or niobium-containing oxide supports which are used in the practice of this invention are oxides having surface areas of from 1 to 200 m²g$^{-1}$, preferably 10 to 100 m²g$^{-1}$, most preferably 25 to 100 m²g$^{-1}$. The oxide supports may be in any convenient form, typically powders, granules, extrudates, castings, rings, chips, beads, spheres, pellets, etc. The supports are typically selected from the group consisting of oxides of tantalum, oxides of niobium, $Al_2O_3$-$Ta_2O_5$, $Al_2O_3$-$Nb_2O_5$, $SiO_2$-$Ta_2O_5$, $SiO_2$-$Nb_2O_5$, $Ta_2O_5$-Carbon, $Nb_2O_5$-Carbon, alkaline earth-tantalum oxides, alkaline earth-niobium oxides, alkali-tantalum oxides, alkali-niobium oxides, rare earth-tantalum oxides, rare earth-niobium oxides, Group IVb-tantalum oxides, Group IVb-niobium oxides, and mixtures thereof. Preferably, the supports are tantalum oxides or niobium oxides or mixtures thereof or admixed with alumina, silica, or Group IVb oxides. Most preferably, the support is essentially pure $Ta_2O_5$ or $Nb_2O_5$. With most supported metal catalysts, the higher the surface area of the support, the higher the dispersion of the supported metal at a given metal loading. It is therefore desirable to use tantalum oxides or niobium oxides or tantalum or niobium-containing oxides (preferably $Ta_2O_5$ or $Nb_2O_5$) with as high a surface area as possible to maximize the dispersion of the metal. Nickel is deposited on the chosen support in a concentration of from about 0.01 to 75 wt. %, preferably from 1 to 10 wt. %. The nickel deposited on the chosen support possesses a particle crystallite size as determined by standard techniques, such as X-ray diffraction or transmission electron microscopy, of from 1 to 30 nm, preferably 1 to 10 nm, most preferably 1 to 5 nm.

Such supported nickel catalysts exhibit selectivity to paraffinic hydrocarbon products of from 2 to 6 carbons inclusive which are substantially free of olefins and oxygenated products. These catalysts also exhibit reduced methane formation as compared to prior art nickel catalysts (nickel or $Al_2O_3$, nickel on $SiO_2$, nickel on carbon).

The nickel catalysts employed in the practice of the instant process are themselves prepared by techniques known in the art for the preparation of other catalyst systems. A suitable nickel salt, such as nickel nitrate, nickel acetate, etc., is dissolved in a convenient solvent such as water or any suitable solvent and stirred with the chosen support oxide system. After thorough mixing, the mixture is either allowed to dry and then heat treated in air at a temperature of from 100° to 150° C. or alternatively it may be dried in a single step by heating in air at a temperature of between 100° to 150° C. for several hours.

In a preferred embodiment, the nickel catalyst, prepared as outlined above, or by similar or equivalent techniques, is heat treated in a reducing atmosphere, such as hydrogen or a hydrogen-containing gas at a temperature of at least 375° C., preferably at least 425° C. for from typically 0.5 to 4 hours, preferably 1 to 2 hours. U.S. Ser. No. 771,396 filed Feb. 23, 1977, now U.S. Pat. No. 4,149,998 (Tauster, Murrell and Fung) teaches the procedures of preparing catalysts by this method and is hereby incorporated by reference.

It should be noted that this heat treating reduction step need not be practiced as a separate step, since the Fischer-Tropsch synthesis is practiced in a reducing atmosphere and will have a similar reducing effect on the catalyst as the above step.

EXAMPLES

Preparation of 1% Ni/Nb$_2$O$_5$

Nb$_2$O$_5$ was impregnated, using the method of incipient wetness, with an aqueous solution of Ni(NO$_3$)$_2$.6-H$_2$O of such concentration as to provide 1% (wt.) of nickel (calculated as the metal) in the finished catalyst. The impregnate was dried at about 110° C., then reduced in situ in flowing H$_2$ at 450° C. for 1 hour.

Preparation of 1% Ni/Ta$_2$O$_5$

Same as above except substitute Ta$_2$O$_5$ for Nb$_2$O$_5$.

TABLE I

Nickel on Tantalum Oxide Catalysts Show Increased Activity for Hydrocarbon Synthesis from CO and H$_2$ Mixtures

| | Overall Rates ($\mu$ moles/min/g of Ni) | | Specific Rates (Reactions/site/sec) | |
|---|---|---|---|---|
| | CH$_4$ | CO | CH$_4$ | CO |
| 1% Ni/Ta$_2$O$_5$ | 636 | 1434 | 0.051 | 0.115 |
| 1% Ni/Al$_2$O$_3$ | 516 | 618 | 0.011 | 0.013 |

T = 250° C.; P = 1 ATM; H$_2$/CO = 3

TABLE II

Nickel on Niobium Oxide Catalysts Show Increased Activity for Hydrocarbon Formation from H$_2$ and CO Mixtures

| | Rate of Methane Formation ($\mu$ moles/min/g of Ni) | Rate of CO Conversion (moles/min/g of Ni) |
|---|---|---|
| 1% Ni/Nb$_2$O$_5$ | 1080 | 2268 |
| 1% Ni/Al$_2$O$_3$ | 516 | 618 |

T = 250° C., P = 1 ATM, H$_2$/CO = 3

TABLE III

Selectivity of Nickel Catalysts (Reaction Conditions: H$_2$/CO = 3, Pressure = 103 kPa)

| Catalyst | Temp. (°C.) | % CO Conv. | Products (Wt. %) | | | | | |
|---|---|---|---|---|---|---|---|---|
| | | | C$_1$ | C$_2$ | C$_3$ | C$_4$ | C$_5$ | C$_6$ |
| 1% Ni/Ta$_2$O$_5$ | 275 | 11.1 | 58 | 17 | 14 | 7 | 4 | trace |
| 1% Ni/Nb$_2$O$_5$ | 276 | 6.4 | 60 | 18 | 13 | 6 | 3 | trace |
| 1% Ni/Al$_2$O$_3$ | 273 | 6.6 | 88 | 9 | 3 | — | — | — |
| 1% Ni/Ta$_2$O$_5$ | 266 | 8.1 | 50 | 18 | 16 | 10 | 6 | trace |
| 1% Ni/Nb$_2$O$_5$ | 268 | 4.9 | 54 | 20 | 15 | 7 | 4 | trace |
| 1% Ni/Al$_2$O$_3$ | 268 | 4.5 | 87 | 11 | 2 | — | — | — |
| 1% Ni/Ta$_2$O$_5$ | 257 | 6.6 | 45 | 19 | 17 | 12 | 8 | trace |
| 1% Ni/Nb$_2$O$_5$* | 258 | 8.3 | 48 | 18 | 17 | 9 | 8 | trace |
| 1% Ni/Al$_2$O$_3$ | 262 | 3.2 | 88 | 12 | trace | — | — | — |
| 1% Ni/Ta$_2$O$_5$ | 249 | 3.4 | 40 | 20 | 17 | 16 | 7 | trace |
| 1% Ni/Nb$_2$O$_5$* | 250 | 7.2 | 47 | 20 | 17 | 9 | 7 | trace |
| 1% Ni/Al$_2$O$_3$ | 252 | 1.9 | 88 | 12 | trace | — | — | — |

All reactions were conducted at about 2400 hr$^{-1}$, except those with *, which were conducted at 1200 hr$^{-1}$.

What is claimed is:

1. A process for the enhanced synthesis of paraffinic hydrocarbons of from 2 to 6 carbon atoms inclusive with reduced production of methane comprising the steps of passing H$_2$ and CO in an H$_2$/CO mole ratio of from about 0.1 to about 10 over a catalyst reduced at a temperature of at least 375° C. comprising nickel on a tantalum or niobium-containing oxide support wherein said tantalum or niobium-containing oxide support is selected from the group consisting of tantalum oxides, niobium oxides, Al$_2$O$_3$-Ta$_2$O$_5$, Al$_2$O$_3$-Nb$_2$O$_5$, SiO$_2$-Ta$_2$O$_5$, SiO$_2$-Nb$_2$O$_5$, Ta$_2$O$_5$-carbon, Nb$_2$O$_5$-carbon, alkaline earth-tantalum oxides, alkaline earth-niobium oxides, alkali-tantalum oxides, alkali-niobium oxides, rare earth-tantalum oxides, rare earth-niobium oxides, Group IVb-tantalum oxides, Group IVb-niobium oxides, and mixtures thereof, at a space velocity of from about 100 hr$^{-1}$ to about 50,000 hr$^{-1}$, at a temperature of from about 100° C. to about 500° C., at a pressure of from about 100 to about 1×10$^5$ kPa, for a time sufficient to effect the generation of the desired paraffinic product, wherein the concentration of said nickel in said catalyst is from about 0.01 to about 75 wt. %.

2. The process of claim 1 wherein the tantalum-containing oxide support is Ta$_2$O$_5$.

3. The process of claim 1 wherein the niobium-containing oxide suport is Nb$_2$O$_5$.

4. The process of claim 1, 2 or 3 wherein the H$_2$/CO mole ratio is from about 0.5 to about 4, the temperature ranges from about 150° C. to about 400° C., the pressure is from about 100 to about 3100 kPa.

5. The process of claim 1, 2 or 3 wherein the nickel loading is from about 0.01 to about 30 wt. %.

6. The process of claim 4 wherein the nickel loading is from about 0.01 to about 30 wt. %.

7. The process of claim 1, 2 or 3 wherein the H$_2$/CO mole ratio is from about 1 to about 3, the temperature is from about 150° C. to about 300° C., the pressure is from about 100 to about 2100 kPa.

8. The process of claim 1, 2 or 3 wherein the nickel loading is from about 0.1 to about 5.0 wt. %.

9. The process of claim 4 wherein the nickel loading is from about 0.1 to about 5.0 wt. %.

10. The process of claim 7 wherein the nickel loading is from about 0.1 to about 5.0 wt. %.

11. The process of claim 1, 2 or 3 wherein the nickel on support has a total BET nickel surface area of from 10 to 60 m$^2$/g with a nickel crystallite size of less than 5 nm.

12. The process of claim 4 wherein the nickel on support has a total BET nickel surface area of from 10 to 60 m$^2$/g with a nickel crystallite size of less than 5 nm.

13. The process of claim 7 wherein the nickel on support has a total BET nickel surface area of from 10 to 60 m$^2$/g with a nickel crystallite size of less than 5 nm.

14. The process of claim 9 wherein the nickel on support has a total BET nickel surface area of from 10 to 60 m$^2$/g with a nickel crystallite size of less than 5 nm.

15. The process of claim 10 wherein the nickel on support has a total BET nickel area of from 10 to 60 m$^2$/g with a nickel crystallite size of less than 5 nm.

* * * * *